United States Patent [19]
Kirsch

[11] Patent Number: 4,793,808
[45] Date of Patent: Dec. 27, 1988

[54] ENOSSAL IMPLANT

[76] Inventor: Axel Kirsch, P.O. Box 11 68, 7024 Filderstadt 4, Fed. Rep. of Germany

[21] Appl. No.: 865,680

[22] Filed: May 22, 1986

[30] Foreign Application Priority Data

Sep. 3, 1985 [DE] Fed. Rep. of Germany ....... 3531389

[51] Int. Cl.⁴ ............................................... A61C 8/00
[52] U.S. Cl. .................................. 433/173; 433/201.1
[58] Field of Search ............. 433/169, 173, 174, 201.1

[56] References Cited

U.S. PATENT DOCUMENTS

| | | | |
|---|---|---|---|
| 3,473,222 | 10/1969 | Kester | 433/173 |
| 3,589,011 | 6/1971 | Sneer | 433/174 |
| 3,708,883 | 1/1973 | Flander | 433/174 |
| 3,732,621 | 5/1973 | Bostrom | 433/174 |
| 3,863,344 | 2/1975 | Pillet | 433/173 |
| 4,011,602 | 3/1977 | Rybicki | 433/173 |
| 4,446,579 | 5/1984 | Inamori | 433/201.1 |
| 4,474,556 | 10/1984 | Ellis | 433/173 |
| 4,518,357 | 5/1985 | Brinkmann | 433/173 |
| 4,552,532 | 11/1985 | Mozsary | 433/174 |
| 4,568,285 | 2/1986 | Chiaramonte | 433/173 |
| 4,609,354 | 9/1986 | Koch | 433/173 |

FOREIGN PATENT DOCUMENTS

| | | | |
|---|---|---|---|
| 0106815 | 4/1984 | European Pat. Off. | 433/173 |
| 2413883 | 9/1975 | Fed. Rep. of Germany | 433/173 |
| 1034734 | 8/1983 | U.S.S.R. | 433/174 |

Primary Examiner—Gene Mancene
Assistant Examiner—Adriene J. Lepiane
Attorney, Agent, or Firm—Hill, Van Santen, Steadman & Simpson

[57] ABSTRACT

The invention involves an enossal implant with comprehensive fastening devices for a firmly seated but, if necessary, removable tooth replacement that includes a fastening head and a implant post that can be connected to a base body. According to the invention, the fastening head is fitted with a tapering fitting surface in the direction of the tooth replacement; in particular, a conical surface, by which a reliable connection between the fastening head and the tooth replacement is obtained. Preferably, the fastening head can be rotated with respect to the base body, as with a ball-and-socket mechanism.

8 Claims, 2 Drawing Sheets

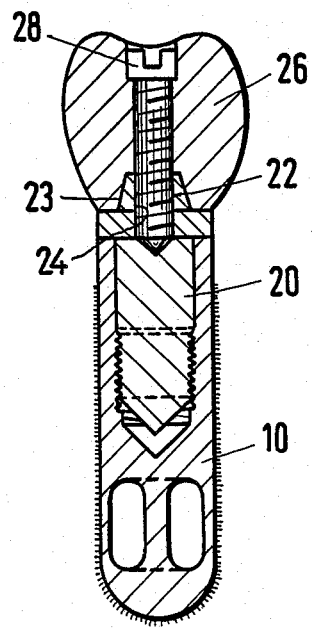
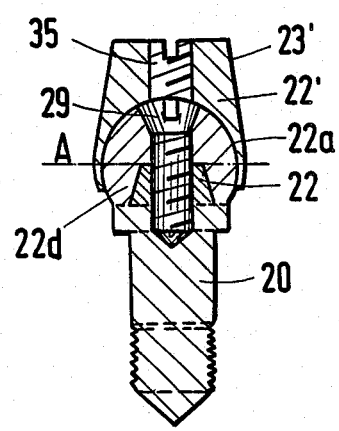
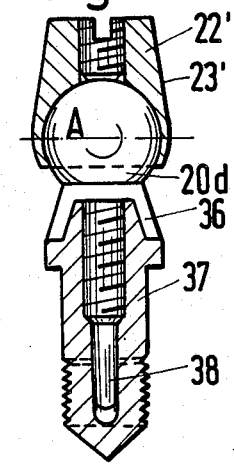
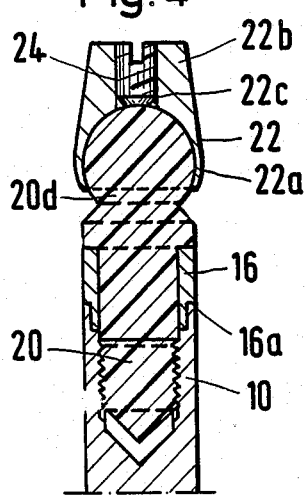
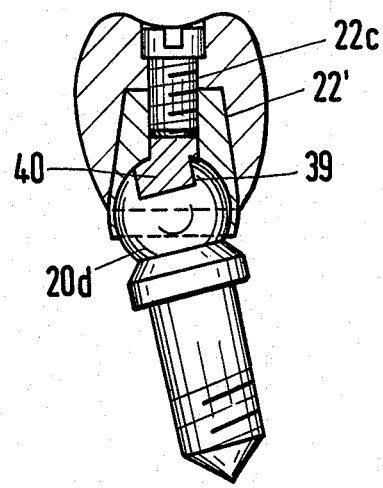
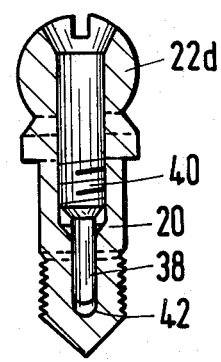
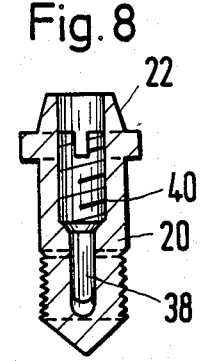

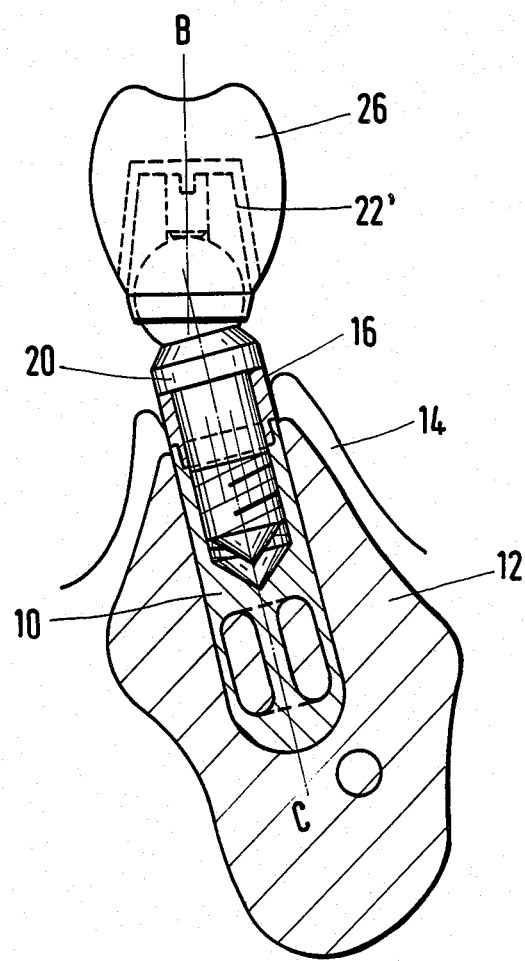

ENOSSAL IMPLANT

FIELD OF THE INVENTION

The field of the invention is that of enossal implants.

BACKGROUND OF THE INVENTION

Enossal implants, also known as endosteal or endosseous implants, are being applied to an increasing extent in order to establish a long-lasting partial or full prosthesis in the jaw of the patient. In this way, a fully functional tooth replacement is provided, which enables the patient to chew food without difficulty, thus fulfilling a very important health function. Thorough chewing, particularly of raw foods and relatively tough foods such as whole-grain bread, is an important preliminary stage in the digestive process. It must be considered that a poorly seated partial or full prosthesis is accompanied by the risk that, due to chewing difficulties, the patient will not consume sufficient quantities of physiologically important foods such as fresh salads, fruit, and vegetables.

In known implants, the tooth replacement is bolted with a fastening head, in which a screw, starting from the chewing surface of the tooth or denture, is screwed into a prepared threaded bore of the fastening head.

It has been demonstrated that a simple screw connection of this type is not adequate in many cases to secure the tooth replacement to the fastening head, since the screws have the tendency to loosen due to the alternating loads of chewing motions, so that the patient has to seek out his dentist to have the tooth replacement newly fastened. Particularly disturbing is when the loosening screw connection involves a single tooth since the tooth can twist, leading to damage to the tooth and/or to its opposite situated tooth.

SUMMARY OF THE INVENTION

An objective of the invention is to produce an improved implant, in which no danger exists that the screw connection between the tooth replacement and the fastening head will loosen.

This objective is fulfilled by the fact that the provision of a fastening head attached to a first end of the implant post, the first end being that end of the implant post which is turned away from the base body. The fastening head is fitted with a fitting surface tapered in the direction of the tooth replacement.

High frictional forces between the fitting surface and the opposite surface in the tooth replacement, due to a tapered fitting surface on the fastening head, on the one hand, and a corresponding opposite surface in the tooth replacement on the other hand, are achieved when mounting the tooth replacement. These frictional forces prevent later relative motion between the tooth replacement and fastening head, so that undesired loosening of the fitting connection can no longer occur, largely due to the wedge effect of the fitting connection which can be additionally secured by a adhesive or screw connection between the fastening head and the tooth replacement.

It has been shown to be advantageous if the fitting surface has a conical surface tapered in the direction of the tooth replacement and mates with a corresponding cone/taper surface on the tooth replacement. This type of conical surface can be relatively large and, additionally, provides a method of centering the tooth replacement in relation to the fastening head.

It has further been shown to be favorable if the implant post is detachable and can be connected to the base body by means of an elastic, deformable middle element. This way, the risk of relative motions between the tooth replacement and the fastening head are further reduced since the forces acting on the tooth replacement are taken by the elastic deformation of the middle element, so that the fitted connection cannot loosen.

In regard to the elastic, deformable middle element, it is preferably manufactured from a viscous-elastic synthetic, which, in conjunction with geometrical measurements of the middle element, permits simulation of the natural tooth movement between the base body healed into the jaw bone and the tooth replacement, or in some cases, the implant post.

The implant post can also be manufactured as part of a one-piece fastening head from a similar viscous-elastic synthetic, in which case the implant post is so constructed that its elastic deformation due to acting forces is essentially outside the elastic range of the fastening head, so that relative motions between the tooth replacement and the fastening head are kept to a minimum. This is not essential, however, in view of the durability of the screw connection, since the deformability of the implant post or fastening head material results in a particularly close fit or wedging of the fitting surfaces, and the smallest tolerances between the fitting surfaces are themselves fully balanced out by the corresponding deformation of the synthetic material during the installation of the screw connection.

In regard to making the connection between the base body and the implant post, a number of advantageous possibilities exist according to the invention.

In one method, the implant post and/or middle element has a cylindrical or slightly conical surface on the end facing the base body, in order to anchor the implant post in the base body. In this case, similar fitted connection can be applied as in the case of the fastening head and tooth replacement.

Another advantageous possibility is to bolt the implant post, or as applicable, the inserted middle element, to the base body. Such a screwed connection is particularly secure if, in addition, mating fitted surfaces are provided on the base body and the implant post or middle element.

Another configuration of the invention provides the possibility of a bayonet type connection between the implant post/middle element and the base body. In this case, the elasticity of the middle element and/or the implant post is ensured by the axial mobility of the elements of the bayonet connection.

Otherwise, the following is to be noted in regard to anchoring the implant post:

If the invention preferably involves an enossal implant, in particular where the implant post is connected by means of a middle element to an invention-specific base body, it is quite possible to apply other implants or natural tooth roots as the base body, particularly with the use of implant posts with cylindrical or slightly conical fitting surfaces. In the latter case of natural tooth roots, these must be provided with cylindrical or slightly conical surfaces by means of cement or glue or alone through frictional forces in order to create the conical fit of the required connection. In addition, a bayonet type connection between the implant post and the base body healed into the bone has proven to be particularly favorable, as is further detailed below.

In development of the invention, it has proven to be advantageous to use a spacer bushing which has a center band and is installed in the open upper end of the base body after it has healed, and thereby provides a shoulder on the upper edge of the base body. By means of the spacer bushing, an extension of the base body is obtained, which is very advantageous for several reasons which are further detailed below.

An implant, according to this invention, with a base body, a spacer bushing, an elastic deformable middle element, and an implant post with fastening head, proceeds such that the metal base body is allowed to heal into the bone in an exact fitting boring of the jaw-bone. Bordering on the boring, one or more slit shaped extensions may be provided for accepting lateral wings of the, in principle, cylindrical base body. The spacer bushing with center band is then installed in the healed-in base body of the implant, such that its shoulder rests on the upper edge of the base body. Then, the elastic deformable middle element, with a shoulder that rests on the upper edge of the spacer bushing, is screwed into the female thread of the base body. Subsequently, the implant post, which rests with one shoulder on the upper side of the middle element and above the shoulder is fitted with a fastening head with a preferably conical fitting surface, is screwed into the middle element. The fastening head has a threaded boring, into which, for example, a crown may be screwed, whereby the fastening screw grasps the crown material starting from the chewing surface and screws into the female thread of the fastening head. The fastening head of the implant post serves to fasten the tooth replacement, which can be a single tooth (a crown), a bridge or a partial or full prosthesis. One or more additional implants are used to fasten larger partial or full prostheses. A particular advantage of the spacer bushing, in this case, is the fact that it extends the base body, which heals into the gums, past the upper edge of the gums, so that they are not irritated by the deformation motions allowed by the elastic deformable middle element.

In the implant according to this invention, the implant post may be replaced by an impression post during the creation of an impression of the jaw and/or teeth, necessary for preparing the tooth replacement. The middle element and spacer bushing are also replaced with this impression post.

It has been shown that during the preparation of a model in the dental laboratory on the basis of such an impression, the axis of the fastening head, already fixed by the axis of the rigid, healed base body, is usually not optimal. The fastening head should be exactly in the middle of the chewing surface of the tooth, if possible. On the other hand, since the tooth replacement must be properly positioned in relation to the patient's other teeth or previous tooth replacements, often there has been no other choice than to place the screw in another, less favorable location on the tooth replacement. Also, attempts to solve this problem by using a deformable collar between the base body of the implant and the fastening head have not been successful, since the collar is often inclined to undesirable deformations later during loading of the tooth replacement.

Starting with the above described difficulties, an additional objective of the invention is to provide a simple method for optimally positioning the longitudinal axis of the fastening head in relation to the longitudinal axis of the base body during work on the model, that is, during exact positioning of the tooth replacement in view of the tooth and jaw relationship of the particular patient.

This objective is solved in an advantageous manner in that the fastening devices are fitted with a ball and socket joint with a ball part and a socket that can swivel in relation to the ball.

It is an advantage of an implant according to this invention that a fine adjustment of the fastening head relative to the base body can be achieved with the aid of the ball-socket joint, so that divergences between the base body axis and the required position of the fastening head can be corrected. This was previously not possible since, on the one hand, the positioning and orientation of the base body and fastening head were firmly predefined, while, on the other hand, the positioning of the tooth replacement and the fastening head permitted no fine adjustment. (In principle, the ball joint could, for example, be connected in one piece with the base body of the implant; such a configuration would hardly find application in practice, since it has proven advantageous to fasten the fastening head to the base body of the implant only after it has healed rigidly into the bone.)

In an advantageous configuration of the invention, an implant includes a ball joint at the end of the implant post turned away from the base body. The implant post has a fastening head and the system includes fastening devices in the form of a detachable, deformable middle element connected to the base body. This is best accomplished when the end of the implant post turned away from the base body is fitted with the ball part that is connected detachably to the tooth replacement. This type of configuration allows the possibility during modeling to optimally locate the axis of the fastening head for fastening the tooth replacement to the base body, on the one hand, and optimally positioning it in relation to natural teeth or other implants, on the other, or also for exact fitting of a single tooth. When the correct axis position of the fastening head is found, then the socket is rigidly attached to the ball part; the ball joint is actually blocked in connection with orienting the axis of the fastening head.

There are basically several methods for establishing a movable connection between the ball part and socket part. For example, a screw connection may be used that allows a prescribed free play within limits and thereby adjustable positioning of the ball and socket, which is then fixed by tightening the screw in the desired position. It is particularly favorable if the socket part is form fitted to the ball part in such a way that the socket is bent radially inwards by shaping with a rolling tool. It can then grasp from behind the mid-axis (equator) of the ball part. In this manner, a one-piece construction of the socket is possible and the ball joint thus requires a total of two elements, namely the ball part and the socket part. Aside from deforming the socket part, there are other methods for creating a form fit between the ball and socket. For example, the socket can be placed on the ball on one side and, in this position, can be connected by another piece on the other side underneath the ball part by bolting, for example.

According to a preferred application of the invention, the socket part is further fitted with a threaded bore which when connected to a set screw establishes a predefined angle to the ball part, which can be changed by loosening the set screw. This solution has the advantage that the threaded bore can be easily created and that the fastening of the set screw can also serve to fasten the tooth replacement, so that a relatively simple, short screw for fastening the ball joint is required. The fastening screw can itself serve as the set screw, where applicable.

A particularly favorable application of an implant according to the invention results when the implant post itself is an elastic deformable piece (within certain limits) made from synthetic material, on which the ball part is formed in one piece so that this part of the ball joint also has a certain elastic deformability. This can be used to limit the relative motion of the bill socket, before locking of the ball element with a set screw for example, to the point that no undesired change in position can occur after positioning of the socket in relation to the ball. Additionally or instead of the above, it is also possible to so construct the socket that it grasps the ball part with a certain preload, where the inner or lower end of the socket is fitted similarly like a clamping sleeve with pretensioned fingers with springs against the ball's upper surface. With this configuration, it is also possible to lock the elements of the ball joint detachably together, for example by means of a spring clip, so that the fingers are prevented from an undesired separation due to tensile forces, and are held in position on the perimeter of the ball part.

These and other details and advantages of the invention are further illuminated by the drawings that follow.

BRIEF DESCRIPTION OF THE DRAWINGS

FIG. 1 is an axial section of the preferred implementation of an implant according to the invention;

FIGS. 2-4 are axial sections of modified applications of fastening devices for the implant post for an implant according to the invention;

FIG. 5 is an axial section of an installed base body in the jaw bone by means of an implant according to the invention with fastening devices according to FIG. 4;

FIGS. 6-8 are axial sections of modified applications of the fastening devices for the implant post for an implant according to the invention.

DETAILED DESCRIPTION OF THE PREFERRED EMBODIMENTS

In detail, FIG. 1 shows an implant according to the invention with a base body 10. The implant is installed precisely in a prepared boring of the patient's jaw bone and heals into the bone in a period of about three months. The base body 10 consists preferably of titanium and is highly polished on its upper end, while the lower part, as shown in FIG. 1, preferably has a roughened surface which can be achieved by knurling or sand blasting, or also by plasma coating with titanium or hydroxyapatite. The base body 10 is open at the upper part and is fitted with a female thread, in which in this example the implant post 20 is directly screwed in, whose shaft in part exhibits a male thread which grasps the female thread of the base body 10 and at its upper end exhibits a fastening head 22, which is fitted with a conical fitting surface 23 and female thread 24. A tooth 26 is fitted on the fastening head 22, which is secured by means of a screw 28, whose shaft grasps the female thread 24. The implant post 20 can also, for example, be fabricated from titanium, but is preferably, for previously mentioned reasons, made from a viscous-elastic synthetic with the appropriate elastic properties and dimensions. The essential advantage of the implant according to FIG. 1 is that the conical surface 23 with a corresponding fitting surface of the tooth replacement or tooth 26 forms a strong frictional and form fitting connection, which after tightening of the fastening screw 28 prevents loosening of the same.

In the embodiment according to FIG. 2 of the drawing, a ball part 22d is fastened by means of screw 29 to the fastening head 22 of the implant post 20. The ball part 22d has a conical recess for acceptance of the socket 22. In this case, the fastening head 22 does not serve directly as the fastener of the tooth replacement as in the embodiment in FIG. 1, but indirectly by keeping the ball part 22d in place, which works together with the socket 22a, which is part of the external fastening head 22', which again has a conical fitting surface 23', ensuring secure retention of the tooth replacement. It should be mentioned here that the availability of a fitting surface 23/23' on the fastening head 22/22', and particularly a conical fitting surface, also permits a favorable and reliable fastening of the tooth replacement even when it is not screwed in as previously described but glued or cemented. The ball part 20d forms an element of the ball joint with which the socket 22a of the external fastening head 22' works as the other element.

The fastening head 22 consists preferably of titanium and has a ball socket 22a which grasps the ball part 22d in such a way that equatorial plane A of the ball part is grasped from behind by the inner or lower edge of the external fastening head 22'. This is accomplished simply by rolling inward the lower edge of the metal fastening head 22', as shown in FIG. 2. Above the socket 22a, the fastening head has a conical head piece 22b with a central threaded bore 22c, in which the set screw 35 is screwed, and can tightened against the ball 22d in order to block the ball joint so that the correct orientation of the elements 22d and 22a of the ball joint is achieved. A tooth or crown 26 can then be placed on the fastening head 22' and held in place by friction or by cement. If screw 35 is implemented as a screw, the upper part of the thread can be used in the fastening head 22 for a retaining screw 28 for the crown 26. If the length of the fastening screw 28 is carefully specified, this same screw can be used both to fasten the crown 26 and also the ball joint. In any case, it is advantageous, if care is taken, that the inner end of the screw 28 or 35 forms a concave calotte shell and that the head of screw 29 forms a convex calotte shell. Blockage of the ball joint is made possible in this way without incurring perpendicular forces which have the tendency to alter the adjusted positions of the joint parts during ball joint blockage.

The example in FIG. 3 corresponds to the one in FIG. 2 to the extent that also in this case a ball joint is used and constructed in the same manner as described in the description for FIG. 2. Different from the example in FIG. 2 is the fact that the conical recess is not located directly in the ball part 20d, but rather in a pedestal part 36 connected to the ball part 20d. This pedestal part rests on the inner fastening head 22. In addition, the ball part is fitted with a screw part 37, whose upper end is preferably installed by press fit into the ball part 20d, and on whole lower end or inner end an expansion bolt 38 is connected. The expansion bolt's diameter is slightly larger than the diameter of the smooth walled extension of the internal thread of the implant post 20. The expansion bolt 38 presses the external thread of the implant post 20 into close contact with the internal thread of the base body 10, so that also a particularly secure connection is maintained between the base body and implant post, whereby it is assumed that the implant post 20 consists of a synthetic elastically deformable material.

A deviation from the application example shown in FIG. 2 is shown in the example in FIG. 4, where the ball part 20d is formed as one piece with the implant post 20. This way, the need for a fastening device to attach the ball part 20d to the implant post is eliminated.

In addition, the implant post 20 according to FIG. 4 is designed for use with a spacer bushing 16, which forms an extension of the upper end of the base body 10. The spacer bushing 16 has a central band, which grasps the base body 10 and ends in a shoulder 16a, which rests on the frontal surface of the base body 10.

FIG. 5 shows an implanted implant according to the invention with an implant post construction according to the previously described FIG. 4. In regard to FIG. 5, the following describes how an implant according to the invention should be handled. In detail, the treatment of the patient begins by fitting the cylindrical base body 10 into a precisely prepared fitting in the jaw-bone 12, which is allowed to heal for a period of three months. During the healing process, the upper, open end of the base body is sealed with a sealing screw (not shown), over which the opened gum tissue 14 again grows. When the base body 10 has healed, the gum is opened in the location of the sealing screw and the spacer bushing 16 is installed in the open end of the base body, which grasps the base body with a band and rests with its shoulder 16a on the upper edge of base body 10. Next, a impression post (not shown) is screwed into the female thread of the base body. When this has occurred, an impression or mold of the tooth/jaw formation of the patient is made and a model is created. On the basis of the model, the appropriate tooth replacement is prepared; in the simplest case, a crown, whereby the implant post used in the model has a ball joint according to FIG. 5 on its upper end which aids in orienting tee fastening head 22 correctly. In this case, locking of the ball joint is done already on the model, after which the various parts of the tooth replacement are brought into their proper position. As shown in FIG. 5, axis C of the base body and axis B of the fastening head form an obtuse angle.

According to FIG. 6, the base body 10 is again extended by means of a spacer bushing 16, and the implant post 20 is again a one-piece synthetic material with a built-in ball part 20d. The ball part includes in its upper part a recess 39, which is connected to the threaded bore 22c of the fastening head 22.

When the proper position of the ball joint is found, a hardening material, for example in the form of balls 40, is introduced through the threaded bore 22c into the recess 39 and neighboring part of the threaded bore 22c. When the hardening material has hardened, the result is that the ball joint is blocked into the desired position.

FIGS. 7 and 8 finally present further variations on the implant post configuration, which correspond somewhat to FIGS. 1 and 4. In both cases, however, a screw 42 is fitted, which similar to the screw part 37 in FIG. 3, has an expansion bolt 38, which grasps into a narrow pocket, or in some cases, into a boring 42, which extends all the way to the inner end of the implant post.

According to the examples of FIGS. 7 and 8, the screws 40 with their expansion bolts 38 serve solely to press the synthetic material of the implant post 20 outwards in the area of the expansion bolt 38 in such a manner that a reliable resistance against turning between the base body and the implant post is ensured.

In summary, an implant made according to the invention, among other advantages, results in shortened labor time for preparation of firmly seated tooth replacements in the laboratory, and increased accuracy and quality, which is beneficial to the patient and represents a significant step forward in dental treatment methods. While embodiments and applications of this invention have been shown and described, it would be apparent to those skilled in the art that many more modifications are possible without departing from the inventive concepts herein. The invention, therefore, is not to be restricted except in the spirit of the appended claims.

what is claimed is:

1. An enossal implant for removably fastening a removable tooth replacement comprising a base body, and an implant post for connection to said base body and for providing a connection for said tooth replacement, wherein the improvement comprises:
   said base body:
   (a) being substantially rigid and elongated;
   (b) having a closed bottom and an open top;
   (c) defining a recess therein;
   (d) defining shoulder means at said top and adjacent said open top for receiving mating shoulder means; and
   (e) having internal thread means in said recess adjacent said bottom;
   there being further provided:
   spacer means:
   (a) which are substantially cylindrical, hollow and have first and second spaced ends;
     (1) said first end constructed for engagement by an implant post; and
     (2) said second end defining shoulder means for mating engagement with said shoulder means on said base body; and
   (b) being removably mounted on said base body;
   said implant post being an elongated member constructed to fit within and extend from said base body and spacer means, said implant post defining a tooth replacement fastening head and cushion means for cushioning forces applied thereto, said post:
   (a) having an elongated body threaded at one end for engagement with said base body threads;
   (b) defining a fastening head at the other end of the post body;
   (c) defining spacer means engaging shoulder means for engaging the first end of said spacer means and urging said spacer means into engagement with said base body and for capturing said spacer means between the base body and the implant shoulder means; and
   (d) having cushioning means between said fastening head and threads for cushioning forces applied to said post.

2. An implant as in claim 1, wherein said implant post is a unitary one-piece viscous-elastic synthetic member.

3. An implant as in claim 1, wherein said fastening head on said implant post has a ball-like shape.

4. An implant as in claim 3, wherein said base body is metallic an at least a portion of said post body is of an insulating material.

5. An implant as in claim 1, wherein said respective base body and spacer shoulder means cooperate and are constructed for centering said spacer means relative to said base body.

6. An implant as in claim 1, wherein said body shoulder means define an internal recess, an external shoulder and an internal shoulder and said spacer shoulder means define an external recess, an external shoulder and an internal shoulder and said shoulder means are constructed to interfit with each other.

7. An implant as in claim 1, wherein said implant post defines an area of reduced cross section adjacent said fastening head for cooperating in flexing and accommodating forces.

8. An implant as in claim 1, wherein said implant post shoulder defines a peripheral radially extending shoulder member for engaging said first end on said spacer means.

* * * * *